(12) United States Patent
Rusu et al.

(10) Patent No.: US 10,254,203 B2
(45) Date of Patent: Apr. 9, 2019

(54) SEPARATION OF PROTEINS

(71) Applicant: MAGTIVIO B.V., CB Heerlen (NL)

(72) Inventors: Viorel Rusu, Eygelshoven (NL); Sven Goethel, Troisdorf (DE)

(73) Assignee: Magtivio B.V., CB Heerlen (NL)

( * ) Notice: Subject to any disclaimer, the term of this patent is extended or adjusted under 35 U.S.C. 154(b) by 0 days.

(21) Appl. No.: 14/658,865

(22) Filed: Mar. 16, 2015

(65) Prior Publication Data

US 2015/0185124 A1   Jul. 2, 2015

Related U.S. Application Data

(63) Continuation of application No. PCT/EP2013/002795, filed on Sep. 17, 2013.

(30) Foreign Application Priority Data

Sep. 17, 2012 (DE) .................. 10 2012 018 234

(51) Int. Cl.
*G01N 1/34* (2006.01)
*C07K 1/22* (2006.01)
*B01D 15/38* (2006.01)

(52) U.S. Cl.
CPC .......... *G01N 1/34* (2013.01); *B01D 15/3885* (2013.01); *C07K 1/22* (2013.01); *Y10T 436/25125* (2015.01)

(58) Field of Classification Search
None
See application file for complete search history.

(56) References Cited

U.S. PATENT DOCUMENTS

| | | | | |
|---|---|---|---|---|
| 5,882,521 A * | 3/1999 | Bouvier | ................ | B01D 15/00 210/198.2 |
| 6,100,079 A * | 8/2000 | Tajima | ............... | C12N 15/1013 435/181 |
| 6,790,668 B1 * | 9/2004 | Ferreira | ................ | G01N 33/94 436/161 |
| 2002/0127739 A1 * | 9/2002 | Pieper | .................... | G01N 30/14 436/515 |
| 2003/0022370 A1 * | 1/2003 | Casagrande | .......... | B01L 3/5085 435/372.1 |
| 2005/0042772 A1 * | 2/2005 | Naylor | .................... | C07K 1/36 436/518 |
| 2013/0217752 A1 * | 8/2013 | Sengupta | ............. | C12N 15/113 514/44 A |

OTHER PUBLICATIONS

English translation of the Written Opinion of the International Searching Authority dated Mar. 31, 2014 for International application No. PCT/EP2013/002795.

Xu, et al. "Synthesis of Magnetic Microspheres with Immobilized Metal Ions for Enrichment and Direct Determination of Phosphopeptides by Matrix-Assisted Laser Desoprtion Ionization Mass Spectrometry." Adv. Mater, 2006, 18, 3289-3293. Published in 2006.

Li, et al. "Cerium Ion-Chelated Magnetic Silica Microspheres for Enrichment and Direct Determination of Phosphopeptides by Matrix-Assisted Laser Desorption Ionization Mass Spectrometry." Journal of Proteome Research 2008, 7, 1767-1777. Feb. 29, 2006.

International Search Report dated Mar. 31, 2014 for International Application No. PCT/EP2013/002795.

Thomas, et al., Determination of Prohibited, Small Peptides in Urine for Sports Drug Testing by Means of Nano-Liquid Chromatography/Benchtop Quadrupole Orbitrap Tandem-Mass Spectrometry, Journal of Chromatography A, 1259 (2012) 251-257.

Saito, et al., Determination of Anabolic Steroids in Human Urine by Automated In-Tube Solid-Phased Microextraction Coupled With Liquid Chromatography-Mass Spectrometry, Journal of Pharmaceutical and Biomedical Analysis 52 (2010) 727-733.

Buchwald, et al. "Validation of an LC-MS/MS method to determine five immunosuppressants with deuterated internal standards including MPA." Buchwald et al. BMC Clinical Pharmacology 2012, 12:2. 11 pages.

Bouzas, et al. Determination of basic drugs of abuse in human serum by online extraction and LC-MS/MS, Anal Bioanal Chem (2009) 395:2499-2507. 9 pages Koenig, Katrin et al. "Deproteination of serum samples for LC-MS/MS analyses by applying magnetic micro-particles." Elsevier. Clinical Biochemistry 46 (2013) 652-655.

* cited by examiner

*Primary Examiner* — Paul S Hyun
(74) *Attorney, Agent, or Firm* — Eschweiler & Potashnik, LLC

(57) ABSTRACT

The disclosure relates to a method for the selective separation of proteins from liquid biological materials which, based on the total quantity, contain a small proportion of one or more trace components, by means of the addition of polar organic solvents having a dipole moment in the range from 1.6 to 4.0 Debye, and adsorption of the proteins on a solid phase carrier, wherein the trace components are separated from the proteins bound to the solid phase carrier by adsorption by means of a) magnetic field, b) centrifugal force, c) gravitational force or d) compressive force, and the trace components remain in the liquid.

20 Claims, No Drawings

SEPARATION OF PROTEINS

REFERENCE TO RELATED APPLICATIONS

This application is a continuation of International Application number PCT/EP2013/002795, filed on Sep. 17, 2013, which claims priority to German Application number 10 2012 018 234.1, filed on Sep. 17, 2012.

FIELD

The disclosure relates to a method for removing (depleting) proteins from liquid biological materials which, based on the total amount, contain a small proportion of a further component or further components (trace components), to biological materials having a low content of proteins and containing the trace component and to the use of the biological materials for, for example, analysis.

BACKGROUND

Biological materials frequently contain a high content of proteins in addition to a low content of further components. When the protein content is high, the components can be qualitatively and analytically detected only with difficulty, for example when checking the medicament level when administering immunosuppressive medicaments or the metabolites thereof from blood, plasma or serum samples.

Liquid biological materials such as plasma samples (and other clinically relevant fluids) are typically tested for the quantitative content of biomarkers (low-molecular-weight, organic compounds) by means of ELISA assays (linked immunosorbent assay) in order to record a disease progression or to diagnose a disease in the first place. In recent years, LC-MS (or LC-MS/MS) has started to establish itself as an alternative to ELISA assays. Typically, for this purpose, the plasma sample is removed from plasma proteins by means of precipitation and subsequent centrifugation and, subsequently, the low-molecular-weight compounds are separated in a reversed-phase LC, quantified (area of the LC graph) and the molar mass analyzed by mass spectrometry (MS).

In this connection, the protein removal is usually carried out manually, since centrifugation steps (or alternatives such as suction through a membrane by means of vacuum or pressure) are difficult to automate.

It is known that, depending on the origin of the sample and the analytical question, the qualitative and quantitative proportion of a trace component from a biological sample can be carried out on different instrument platforms and for different end-applications, such as clinical checks, doping tests, forensic and toxicological reports and tests. Regardless of the technological development for the readout of the experimental data, such as, for example, the technological development in mass spectrometry, a pretreatment of the analytical sample for the purpose of reducing complexity is still necessary.

Fundamentally, the analytical process is divided into five steps from the collection of samples up to the final result:
1) collection of samples,
2) preparation of samples,
3) fractionation of samples,
4) detection of analytes and
5) evaluation of data.

In most cases, a substantial amount of time is expended on steps 1) and 2).

SUMMARY

It is an object of the present disclosure to reduce the protein content in biological materials containing a high content of proteins in addition to a low content of further components, such that the components are accessible for, for example, analytical tests.

DETAILED DESCRIPTION

A method for selectively removing proteins from liquid biological materials is disclosed which, based on the total amount, contain a small proportion of one or more trace components, by adding:
a) polar, organic solvents having a dipole moment within the range from 1.6 to 4.0 debye, and
b) silica gel particles, adsorbing the proteins to the silica gel particles and removing the silica gel particles containing the adsorbed proteins, wherein the trace components remain in the liquid.

Silica gel particles in the context of the present disclosure can, in one embodiment of the disclosure, contain one or more magnetic cores.

In one embodiment of the method according to the disclosure the silica gel particles optionally have one or more magnetic cores and have a diameter within a range from 20 nm to 500 µm. In one embodiment, the silica gel particles contain from 0 to 30 magnetic cores.

The silica gel particles containing the adsorbed proteins can be removed in a magnetic field, or by adsorbing the proteins to nonmagnetic silica gel particles and removing the silica gel particles by means of compression, centrifugal or gravitational force.

Therefore, a method for selectively removing proteins from liquid biological materials is disclosed which, based on the total amount, contain a small proportion of trace components, by adding:
a) polar, organic solvents having a dipole moment within the range from 1.6 to 4.0 debye, and
b) silica gel particles having one or more magnetic cores, adsorbing the proteins to the magnetic silica gel particles and removing the magnetic silica gel particles containing the adsorbed proteins in a magnetic field, or adsorbing the proteins to nonmagnetic silica gel particles and removing the silica gel particles by means of compression, centrifugal or gravitational force, wherein the trace components remain in the liquid.

Liquid biological materials in the context of the present disclosure are, in one embodiment, aqueous human or animal body fluids.

Liquid biological materials in the context of the present disclosure can, for example, be plasma, serum, saliva, teardrops, brain fluid, tissue fluid, amniotic fluid, follicular fluid, whole blood or hemolyzed blood, urine, liquor, such as cerebrospinal fluid, interstitial fluids, but also, for example, fermentation media.

The liquid biological materials are generally aqueous solutions containing not only proteins but also salts and further organic components.

In the context of the present disclosure, the liquid biological materials contain, based on the total amount, a small proportion of further organic components ("trace components"). The proportion of the trace components in the liquid biological materials is, based on the total amount, generally less than 10% by weight. In the context of one embodiment of the disclosure, a proportion of the trace component within the range from 10 E-12 to 5% by weight is contemplated. In particular, a proportion of the trace component within the range from 10 E-9 to 2% by weight is desirable in one embodiment.

Surprisingly, the method according to the disclosure makes it possible to easily and rapidly remove the proteins from the biological fluids without altering the composition and the amounts of the trace components.

Trace components in the context of the present disclosure can, for example, be:

a) anti-inflammatory immunosuppressants, such as, for example, azathioprine, mercaptopurine, mycophenolate, mofetil, mycophenolic acid, sirolimus (rapamycin), leflunomide, teriflunomide, methotrexate, tacrolimus, ciclosporin, pimecrolimus, gusperimus, lenalidomide, etc.

b) antiarrhythmics, such as, for example, procainamide, quinidine, disopyramide A, lidocaine, phenytoin, mexiletine, tocainide, flecainide, propafenone, moricizine, lidocaine, phenytoin, mexiletine, propanolol, esmolol, timolol, metoprolol, atenolol, bisoprolol, sotalol, ibutilide, dofetilide, dronedarone, E-4031, verapamil, diltiazem, adenosine, digoxin, etc.

c) nonprotein biomarkers, such as, for example, estrogens and sex hormones, ascorbic acid, carotenoids, cytokines, etc.

d) drugs, such as, for example, heroin, cocaine, amphetamine, morphine, etc.

e) doping substances, such as, for example, e1) active anabolic ingredients such as anabolic-androgenic steroids (AAS), for example 1-androstenediol, 1-androstenedione, bolandiol, bolasterone, boldenone, boldione, calusterone, clostebol, danazol, dehydrochloromethyltestosterone, desoxymethyltestosterone, drostanolone, ethylestrenol, fluoxymesterone, formebolone, furazabol, androstenediol, androstenedione, dihydrotestosterone, testosterone, clenbuterol, tibolone, zeranol, zilpaterol.

e2) beta-2 agonists, such as abediterol, amibegron, arbutamine, arformoterol, bambuterol, bitolterol, carbuterol, clenbuterol, fenoterol, formoterol, hexoprenaline, indacaterol, isoetharine, isoprenaline, levosalbutamol, olodaterol, pirbuterol, procaterol, epinephrine, ractopamine, reproterol, rimiterol, salbutamol, salmeterol, solabegron, terbutaline, tulobuterol.

e3) hormone antagonists and modulators such as anastrozole, androstatrienedione, exemestane, formestane, letrozole, testolactone, raloxifene, tamoxifen, toremifene, clomiphene, cyclofenil, fulvestrant.

e4) diuretics such as acetazolamide, amiloride, bumetanide, canrenone, chlorthalidone, ethacrynic acid, furosemide, indapamide, metolazone, spironolactone, thiazide, triamterene.

e5) stimulants such as adrafinil, amfepramone, amiphenazole, amphetamine, amphetaminil, benfluorex, benzphetamine, benzylpiperazine, bromantane, clobenzorex, cocaine, cropropamide, crotetamide, dimethylamphetamine, etilamfetamine, famprofazone, fencamine, fenethylline, fenfluramine, fenproporex, furfenorex, mefenorex, mephentermine, mesocarb, methamphetamine, (d-), p-methylamphetamine, methylenedioxyamphetamine, methylenedioxymethamphetamine, methylhexanamine, modafinil, norfenfluramine, phendimetrazine, phenmetrazine, phentermine, 4-phenylpiracetam, prenylamine, prolintane.

e6) narcotics such as buprenorphine, dextromoramide, diamorphine (heroin), fentanyl and its derivatives, hydromorphone, methadone, morphine, oxycodone, oxymorphone, pentazocine, meperidine.

f) mycotoxins, such as, for example, aflatoxin B1, fumonisin B1 and B2, ochratoxin A, patulin and zearalenone.

g) antidepressants, such as, for example, celexa, cipramil, lexapro, cipralex, seroplex, lexamil, prozac, sarafem, symbyax, luvox, paxil, aropax, zoloft, viibryd, pristiq, cymbalta, ixel, effexor, tolvon, remeron, avanza, zispin, strattera, mazanor, sanorex, edronax, vivalan, wellbutrin, zyban, stablon, coaxil, tatinol, amineptine, valdoxan, melitor, thymanax, elavil, endep, anafranil, adapin, sinequan, tofranil, surmontil, norpramin, pamelor, aventyl, noritren, vivactil, marplan, aurorix, manerix, nardil, eldepryl, emsam, parnate, nicotine.

h) antiepileptics, such as, for example, acetazolamide, carbamazepine, clobazam, clonazepam, diazepam, ethosuximide, felbamate, gabapentin, lacosamide, lamotrigine, levetiracetam, mesuximide, midazolam, oxcarbazepine, phenobarbital, phenytoin, pregabalin, primidone, rufinamide, stiripentol, sultiame, tiagabine, topiramate, valproic acid.

i) antipsychotics, such as, for example, aripiprazole, olanzapine, paliperidone, quetiapine, risperidone, ziprasidone, solian, abilify, leponex and/or j) antibiotics, such as, for example, ciprofloxacin, fosfomycin, fusafungine, rifaximin, telithromycin, vancomycin, cephalosporins, macrolide antibiotics, penicillins, sulfonamides and trimethoprim, tetracyclines, ethambutol, isoniazid, myambutol, pyrazinamide, rifampicin, streptomycin, imipenem, cilastatin, meropenem, lincosamides, monobactam.

Particularly preferred trace components for the method according to one embodiment of the disclosure are immunosuppressants, antiarrhythmics, nonprotein biomarkers, doping substances, antidepressants and antibiotics.

Proteins which can be removed in the context of the present disclosure can, for example, be serum albumins, immunoglobulins, fibrinogen, regulator proteins.

In the context of the present disclosure, the liquid biological materials can contain more than 0.1% by weight of proteins.

In the context of one embodiment of the present disclosure, preference is given to a protein content within the range from 0.01 to 25% by weight, and particular preference is given to a protein content within the range from 0.1 to 12% by weight.

The trace components in the context of the present disclosure are generally readily soluble in the polar, organic solvents.

Generally, the solubility of the trace components in the polar, organic solvents is at least 0.1 pg/l, for example, within the range from 1 ng/l to 500 mg/l.

Polar, organic solvents in the context of the present disclosure generally have a dipole moment within the range from 1.6 to 4.0 debye, for example, from 1.69 to 3.96 debye.

Examples of polar, organic solvents are: acetone, acetonitrile, ethanol, methanol, propanol, isopropanol, dimethyl sulfoxide, polyethylene glycol (PEG).

Polar, organic solvents are, in one embodiment: acetone, acetonitrile, ethanol and isopropanol.

The polar, organic solvents can be used individually or in a mixture.

The mixtures are, for example, set such that alcohols such as ethanol and isopropanol are combined in various parts by weight or acetonitrile is combined together with an alcohol such as, for example, isopropanol or ethanol, or combinations of alcohols such as ethanol and isopropanol having various parts by weight are combined with, for example, acetonitrile.

In one embodiment the method according to the disclosure is carried out on an adsorbent composed of silica gel particles having one or more magnetic cores and having a pore size within the range from 2 to 50 nm in one example, from 5 to 30 nm in another example, and an inner surface area within the range from 0.1 to 400 m$^2$/g, or from 10 to 200 m$^2$/g in another example. In the method, the proteins, adsorbed on the silica-gel particles solid phase, are separated from the trace components by applying a magnetic field.

Alternatively, the proteins, after addition of an organic, polar solvent mixture as described above, can be adsorbed to nonmagnetic silica gel particles. In this case, the bound proteins can be separated from the trace components remaining in solution by means of compression, gravitational or centrifugal force.

In the method, the silica gel particles can be in the form of isolated spherical particles, monolithic silica gel phases, or membranes.

Especially in the case of monolithic silica gel phases and silica gel-based membranes, establishing a pressure difference makes it possible to conduct the liquid containing the dissolved trace components through the silica gel material in line with the pressure difference and to separate the liquid from the adsorbed, retained proteins. In this case, the pressure difference is established by means of positive pressure/negative pressure on the membrane/monolithic phase of the membrane or monolithic phase.

The particles generally have a diameter within the range from 20 nm to 500 µm, or from 200 nm to 10 µm in another example, or from 500 nm to 1.3 µm in yet another example.

The adsorbent composed of silica gel particles having a magnetic core can be prepared by coating iron oxide-containing particles with silica gel.

The coating of iron oxide-containing particles with silica gel is known per se (J. Colloid Interface Sci. 1968, 26, 62 to 69; Langmuir 2005, 21, 10763 to 10769; J. Colloid Interface Sci 2005, 283, 392 to 396).

The coating of iron oxide-containing particles with silica gel for the method according to the disclosure can, for example, be carried out as follows:

A suspension of iron oxide-containing particles in an alcohol (e.g., isopropanol) is admixed with tetraethyl orthosilicate (TEOS) under strong stirring in the presence of ammonia for the purpose of coating. The thickness of the coating can be controlled by the amount of the tetraethyl orthosilicate added.

The coated iron oxide-containing particles are washed with an alcohol (e.g., methanol) and stored in water.

For the method according to one embodiment of the disclosure, preference is given in particular to silica gel particles including or consisting of a mesoporous layer which is applied to the magnetic core and has a layer thickness within the range from 10 to 100 nm.

Magnetic cores for the silica gel particles according to the disclosure can be particles which are known per se and which are composed of iron oxide ($Fe_2O_3$) and silicon dioxide, polystyrene and/or polyvinyl alcohol.

For the method according to one embodiment of the disclosure, preference is given to using iron oxide particles having a mesoporous silica gel coating, as arises in the presence of polyethylene glycol as porogenic agent.

Particular preference is given in one embodiment to silica gel particles including or consisting of a mesoporous layer which is applied to the magnetic core and has a layer thickness within the range from 10 to 100 nm, the magnetic cores containing maghemite and/or magnetite within the range from 30 to 95% by weight and having a mean diameter within the range from 10 nm to 500 µm, the silica gel particles having a mean diameter within the range from 20 nm to 500 µm, or from 200 nm to 10 µm in another example, or from 500 nm to 1.5 µm in yet another example.

One embodiment of the method according to the disclosure is characterized in that from 1.5 to 4 parts by weight, or from 2 to 3 parts by weight in another example, of the polar, organic solvent and from 0.02 to 0.50 parts by weight, or from 0.05 to 0.40 parts by weight in yet another example, of the silica gel particles are added to one part by weight of liquid biological materials.

The silica gel particles having a magnetic core can be removed using a magnetic separator.

After proteins have been selectively removed according to disclosure from liquid biological materials, the remaining liquid contains only few proteins, which do not hamper further tests or isolation of the trace components. The proportion of the proteins in the remaining liquid is generally less than 0.0001% by weight.

The method according to the disclosure can, for example, be carried out as in the following acts:
(i) providing liquid biological materials containing one or more trace componenets,
(ii) contacting the liquid biological materials with silica gel particles,
(iii) removing the protein by adding organic solvents in the predefined ratio,
(iv) swirling and incubating the mixture to adsorb the proteins on the surface of the particles,
(v) removing the supernatant, which contains the trace components, from the particles, which contain the adsorbed proteins, by applying a magnetic field or by compression, centrifugal or gravitational forces,
(vi) depleting the supernatant containing one or more compounds, whereby compounds are selectively extracted from the biological sample,
(vii) a further optional act involving the drying of the supernatant by vaporizing the organic solvent mixture at elevated temperature (50-85° C.) and, subsequently, the sample is recollected in a low, defined volume of organic solvent,
(xiii) analyzing one or more compounds from (vi) or (vii) by means of mass spectrometry, it being optionally possible for a further chromatographic separation of the sample to be carried out and/or immunoassays, which can be in monoplex or multiplex format, it being possible for a multiplex immunoassay to be carried out via multicolor particle coding.

The present disclosure also provides biological materials having a low content of proteins and trace components, which materials are characterized in that proteins are removed from liquid biological materials which, based on the total amount, contain a small proportion of a trace component, by adding
a) polar, organic solvents having a dipole moment within the range from 1.6 to 4.0 debye and
b) silica gel particles, by adsorbing the proteins to the silica gel particles, and, after removal of the silica gel particles containing the adsorbed proteins, the trace components remain in the liquid.

In one embodiment of the present disclosure, the biological materials having a low content of proteins and active components are, for example, selected from any of the groups of
a) the anti-inflammatory immunosuppressants
b) the antiarrhythmics
c) the nonprotein biomarkers
d) the drugs
e) the doping substances
f) the mycotoxins g) the antidepressants
h) the antiepileptics
i) the antipsychotics
j) the antibiotics.

The present disclosure also provides for the use of biological materials having a low content of proteins and trace components, for example in analytical tests or preparative studies.

Especially in the analysis of trace components in addition to proteins as main component, the present disclosure advantageously introduces a simple procedure involving minimal errors, which can be caused especially by the complexity of the system.

EXAMPLES

Example 1

Iron Oxide Particles Having a Mesoporous Silica Gel Coating in the Presence of Polyethylene Glycol 10 ml of iron oxide particles (e.g., MagSi-S beads from MagnaMedics) with a concentration of 20 mg/ml are removed in a magnetic field and then dispersed under strong stirring in 30 ml of polyethylene glycol (mean molecular weight 400), 10 ml of isopropanol and 2 ml of water. 2 ml of an ammonia solution (25% by weight) and 0.75 ml of tetraethyl orthosilicate (TEOS) are added to this mixture. The coating takes place within 6 hours under even stirring.

The coated iron oxide-containing particles are washed with 40 ml of water. The final concentration of acid group-free silica gel particles is 20 mg/ml.

Example 2

Sample Preparation for Determining of Cortisol Lyophilized Human Serum

Materials:
Lyophilized human serum containing cortisol
Magnetic beads (300 mg/ml) in acetonitrile according to example 1
Organic solvent mix, 100% acetonitrile
Microtiter plates, UV type with flat bottom
Microplate reader;

1. Lyophilized human serum is resuspended in 1.5 ml of sterile water, and so the final concentration of cortisol is 0.277 µg/ml.
2. 30, 40, 60 and 80 µl of resuspended serum is transferred to microtiter plates (UV-transparent format).
3. 25 µl of MagnaMedics particles solution and then the organic solvent mixture are added to the serum. In this connection, the volume of the organic solvent mixture is twice that of the serum volume.
4. Subsequently, the solution is thoroughly mixed and the reaction volume is incubated at room temperature for 2 min.
5. Prior to the magnet-based collection, the sample is ultrasonically treated for 5 s.
6. The magnetic particles are fully collected in a magnetic separator.
7. The supernatant is removed and measured at 242 nm in microtiter plate format.

Results:

A serum sample which does not contain any cortisol is used as negative control in order to determine the background. The measured optical density (OD) correlates directly with the cortisol concentration.

|  | Serum with cortisol added as additive | | | | Serum without cortisol added as additive |
| --- | --- | --- | --- | --- | --- |
|  | 30 | 40 | 60 | 80 |  |
| Sterile water (µl) | 70 | 60 | 40 | 20 | 0 |
| Magnetic particles (µl) | 25 | 25 | 25 | 25 | 25 |
| Acetonitrile (µl) | 200 | 200 | 200 | 200 | 200 |
| Transfer volume (µl) | 200 | 200 | 200 | 200 | 200 |
| OD at 242 nm | 0.3554 | 0.4229 | 0.6590 | 0.8571 | 0.0948 |
|  | 0.3371 | 0.3670 | 0.5410 | 0.6841 | 0.0687 |
| Mean OD | 0.3462 | 0.3949 | 0.6000 | 0.7706 | 0.8175 |
| Corrected OD | 0.2644 | 0.3131 | 0.5182 | 0.6888 | — |
| Amount of cortisol measured (µg) | 8.31 | 11.08 | 16.62 | 22.16 | — |

The invention claimed is:

1. A method for selectively removing proteins from a liquid biological material, the method comprising:
   adding magnetic silica gel particles to the liquid biological material, wherein based on a total amount of the liquid biological material, less than 10% by weight of the liquid biological material is trace components;
   after adding the magnetic silica gel particles, adding at least one polar, organic solvent to the liquid biological material to form a mixture comprising the liquid biological material, the magnetic silica gel particles, and the at least one polar, organic solvent, the at least one polar, organic solvent having a dipole moment within a range from 1.6 to 4.0 debye, wherein the at least one polar, organic solvent is added in a predefined ratio from 1.5 to 4 parts by weight to one part by weight of the liquid biological material;
   swirling and incubating the mixture to adsorb the proteins of the liquid biological material on surfaces of the magnetic silica gel particles;
   magnetically removing the magnetic silica gel particles containing the adsorbed proteins from the mixture to form a liquid residue, wherein the trace components remain in the liquid residue; and
   subsequently analyzing the liquid residue by mass spectrometry, wherein before the liquid residue is analyzed, drying the liquid residue by vaporizing the liquid residue at a temperature between 50 degree Celsius (° C.) and 85° C.

2. The method as claimed in claim 1, wherein the magnetic silica gel particles have at least one magnetic core.

3. The method as claimed in claim 1, wherein the magnetic silica gel particles have a diameter within a range from 20 nm to 500 μm.

4. The method as claimed in claim 1, wherein the liquid biological material has a high content of proteins and a low content of the trace components.

5. The method as claimed in claim 1, wherein the liquid biological material is selected from the group comprising aqueous human body fluids and animal body fluids.

6. The method as claimed in claim 1, wherein the trace components are soluble in the at least one polar, organic solvent.

7. The method as claimed in claim 1, wherein a minimum concentration of the trace components is 100 pg/l.

8. The method as claimed in claim 1, wherein adding the magnetic silica gel particles to the liquid biological material includes adding 0.05 to 0.4 parts by weight of the magnetic silica gel particles to one part by weight of the liquid biological material.

9. The method of claim 1, wherein the liquid biological material is selected from the group comprising plasma, serum, saliva, teardrops, brain fluid, tissue fluid, amniotic fluid, follicular fluid, whole blood, hemolyzed blood, urine, cerebrospinal fluid, interstitial fluids, fermentation media and mixture and solutions thereof.

10. The method of claim 1, further comprising:
adding the liquid biological material to one of multiple wells of a microtiter plate, wherein each of the multiple wells of the microtiter plate comprise only one opening;
wherein the magnetic silica gel particles are added to the liquid biological material after the liquid biological material is added to the one of the multiple wells; and
wherein the liquid residue remains in the one of the multiple wells after magnetically removing the magnetic silica gel particles containing the adsorbed proteins from the mixture.

11. The method of claim 1, wherein the trace components comprise one or more components selected from the group comprising anti-inflammatory immunosuppressants, antiarrhythmics, nonprotein biomarkers, drugs, doping substances, mycotoxins, antidepressants, antiepileptics, antipsychotics and antibiotics.

12. The method of claim 1, wherein the mixture is incubated for 2 minutes.

13. A method for selectively removing proteins from a liquid biological material, the method comprising:
adding the liquid biological material to a container, wherein based on a total amount of the liquid biological material, less than 10% by weight of the liquid biological material is trace components;
adding magnetic silica gel particles to the liquid biological material in the container;
after adding the magnetic silica gel particles to the liquid biological material, adding at least one polar, organic solvent to the liquid biological material to form a mixture comprising the liquid biological material, the magnetic silica gel particles, and the at least one polar, organic solvent, the at least one polar, organic solvent having a dipole moment within a range from 1.6 to 4.0 debye, wherein the at least one polar, organic solvent is added in a predefined ratio from 1.5 to 4 parts by weight to one part by weight of the liquid biological material;
swirling and incubating the mixture to adsorb the proteins of the liquid biological material on surfaces of the magnetic silica gel particles;
magnetically removing the magnetic silica gel particles containing the adsorbed proteins from the mixture by using a magnetic separator to form a liquid, wherein the liquid remains in the container, and wherein the trace components remain in the liquid; and
subsequently analyzing the liquid by mass spectrometry regarding an occurrence of the trace components, before the liquid is analyzed, drying the liquid by vaporizing the liquid at a temperature between 50 degree Celsius (° C.) and 85° C.

14. The method as claimed in claim 13, wherein adding the magnetic silica gel particles to the liquid biological material includes adding 0.05 to 0.4 parts by weight of the magnetic silica gel particles to one part by weight of the liquid biological material.

15. The method of claim 13, wherein the trace components comprise one or more components selected from the group comprising anti-inflammatory immunosuppressants, antiarrhythmics, nonprotein biomarkers, drugs, doping substances, mycotoxins, antidepressants, antiepileptics, antipsychotics and antibiotics.

16. The method of claim 13, wherein the mixture is incubated for 2 minutes.

17. A method for selectively removing proteins from a liquid biological material, the method comprising:
adding the liquid biological material to one of multiple wells of a microtiter plate, wherein each of the multiple wells of the microtiter plate has only one opening, and wherein less than 10% by weight of the liquid biological material is trace components;
adding magnetic silica gel particles to the one of the multiple wells;
after adding the magnetic silica gel particles to the one of the multiple wells, adding at least one polar, organic solvent to the one of the multiple wells to form a mixture comprising the liquid biological material, the magnetic silica gel particles, and the at least one polar, organic solvent in the one of the multiple wells, the at least one polar, organic solvent having a dipole moment within a range from 1.6 to 4.0 debye;
swirling and incubating the mixture to adsorb the proteins of the liquid biological material on surfaces of the magnetic silica gel particles;
magnetically removing the magnetic silica gel particles containing the adsorbed proteins from the mixture through the one opening of the one of the multiple wells, such that a liquid residue comprising the trace components is formed in the one of the multiple wells; and
subsequently analyzing the liquid residue by mass spectrometry, wherein before the liquid residue is analyzed, drying the liquid residue by vaporizing the liquid residue at a temperature between 50 degree Celsius (° C.) and 85° C.

18. The method of claim 17, wherein the trace components comprise:
an anti-inflammatory immunosuppressant, an antiarrhythmic substance, a nonprotein biomarker, a drug, a doping substance, a mycotoxin, an antidepressant, an antiepileptic substance, an antipsychotic substance, and an antibiotic substance.

19. The method of claim 17, wherein the mixture is incubated for 2 minutes.

20. The method of claim 19, wherein:
the microtiter plate is a UV type microtiter plate, and
each of the multiple wells of the microtiter plate has a flat bottom surface.

* * * * *